United States Patent [19]

Panster et al.

[11] 4,362,885

[45] Dec. 7, 1982

[54] PROCESS FOR THE MANUFACTURE OF (IODOORGANYL)ALKOXYSILANES

[75] Inventors: Peter Panster, Rodenbach; Alfons Karl, Hanau; Wolfgang Buder, Rodenbach; Peter Kleinschmit, Hanau, all of Fed. Rep. of Germany

[73] Assignee: Degussa Aktiengesellschaft, Frankfurt am Main, Fed. Rep. of Germany

[21] Appl. No.: 330,355

[22] Filed: Dec. 14, 1981

[30] Foreign Application Priority Data

Dec. 12, 1980 [DE] Fed. Rep. of Germany ....... 3047995

[51] Int. Cl.$^3$ ............................ C07F 7/08; C07F 7/18
[52] U.S. Cl. ..................................... 556/446; 556/476
[58] Field of Search ................................. 556/476, 446

[56] References Cited

U.S. PATENT DOCUMENTS

| | | | |
|---|---|---|---|
| 2,803,638 | 8/1957 | Holdstock | 556/476 |
| 2,972,638 | 2/1961 | Tiers | 556/476X |
| 3,125,594 | 3/1964 | Hubel et al. | 556/476 X |
| 3,342,898 | 9/1967 | Roselli | 556/476 X |
| 3,449,393 | 6/1969 | Sattlegger et al. | 556/476 |
| 3,897,479 | 7/1975 | Inamoto et al. | 556/476 |

FOREIGN PATENT DOCUMENTS

| | | | |
|---|---|---|---|
| 503881 | 3/1976 | U.S.S.R. | 556/476 |
| 523100 | 8/1976 | U.S.S.R. | 556/476 |

*Primary Examiner*—Paul F. Shaver
*Attorney, Agent, or Firm*—Beveridge, DeGrandi and Kline

[57] ABSTRACT

The subject of the invention is a process for the manufacture of (iodoorganyl)alkoxysilanes of the general formula:

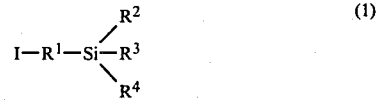

in which $R^1$ is an alkylene group, $R^2$ is an alkoxy group and $R^3$ and $R^4$ an alkoxy group and/or an alkyl or aryl group, whereby the chlorine or bromine compound corresponding to that of formula (1) is caused to react with stoichiometric to double molar quantities of an inorganic iodine donor in the presence of 0.01–5 mol % of an organic substituted onium salt of nitrogen, phosphorus, arsenic or antimony or an organic substituted sulfonium salt or a crown ether as catalyst, in certain solubilizing agents.

6 Claims, No Drawings

PROCESS FOR THE MANUFACTURE OF (IODOORGANYL)ALKOXYSILANES

The present invention relates to a process for the manufacture of (iodoorganyl)alkoxysilanes which permits the preparation of this class of compounds in a substantially shorter reaction time and significantly higher yield than do processes according to the state of the art.

(Halogenorganyl)alkoxysilanes represent valuable chemical reagents. They are used for example for the modification of inorganic carrier materials which have available surface active groups, especially OH groups, for the synthesis of functional (organyl)alkoxysilyl substituted compounds, which include corresponding ammonium compounds used as surface active agents, algicides or bactericides or they represent general intermediate products in the manufacture of other important silanes.

Examples of these applications and uses are described in, among others, European patent application No. 0 008 902; DE-AS No. 10 23 462; U.S. Pat. No. 4,093,642; DE-OS No. 22 22 997; DE-OS No. 24 08 192; and DE-AS No. 21 41 159.

Although from the point of view of reactivity (iodoorganyl)alkoxysilanes would be most suitable for these syntheses, frequently in the past only the chloro or bromoorganyl derivatives have been used. The reason for this is that these halogen compounds were obtained considerably more easily and in higher yield than the iodine homologues, which were normally obtained by halogen exchange; this is described, for example, by M. G. Voronkov et al. in Zhurnal Obshchei Khimii 45, 9, 2010 (1975). According to this teaching, for example, (3-iodopropyl)trimethoxysilane can be obtained after 25 hours reaction in boiling acetone, with an excess of NaI of about 6 mol % in a yield of only 50.7%. Similarly, (3-iodopropyl)triethoxysilane can be obtained after 25 hours reaction in the same solvent with an excess of NaI of 5.5 mol % in only 52.2% yield or (2-iodoethyl)triethoxysilane after 27 hours reaction with an excess of 11 mol % in only 40.9% yield. In other publications in which (iodoorganyl)alkoxysilanes are mentioned, as in U.S. Pat. Nos. 3,390,976 and 3,780,127, acetone is likewise used exclusively in the preparation; yields and reaction times are however given only in the latter patent. The yield cited therein is also quite low, at about 41%.

A process has now been found which allows the preparation of (iodoorganyl)alkoxysilanes of the following formula (I):

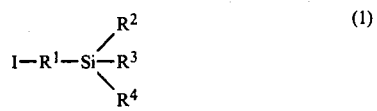

in which $R^1$ represents a straight chain or branched alkylene group having 1 to 20 carbon atoms, a cycloalkylene group having 5 to 8 carbon atoms or units of the type:

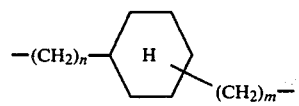

or

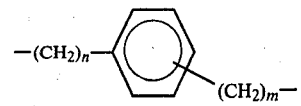

wherein n is a number between 1 and 6 of methylene groups in the chain attached to the halogen and m is a number from 0 to 6, $R^2$ represents an alkoxy group having 1 to 5 carbon atoms, the methoxyethoxy or ethoxyethoxy group, $R^3$ and $R^4$ may be the same or different from each other and may have the same meaning as $R^2$ or represent branched or linear alkyl groups having 1 to 10 carbon atoms, a phenyl group or a phenyl group substituted by a halogen atom, in very short reaction times and high yield and at distinctly lower cost compared with the prior art processes. It was found in fact that the exchange from chlorine or bromine to iodine can be carried out quantitatively with a yield of more than 80% of product in 2 to 8 hours if the corresponding chlorine or bromine compound is caused to react with stoichiometric to double molar quantities of alkali, alkaline earth or ammonium iodide in the presence of 0.02 to 5 mol % of a quarternary ammonium, phosphonium, arsonium, antimonium or tertiary sulfonium salt with alkyl, aryl or aralkyl substituents and an organic or inorganic anion or a crown ether as catalyst in an organic liquid or in a mixture of organic liquids which is substantially inert towards the silane and is able to dissolve at least partly the iodide or silane component.

Preferred examples of usable compounds of this catalyst type, some of which are commercially available, are especially tricapryl(methyl)ammonium chloride ("Aliquat 336") or others such as benzyltrimethylammonium chloride or hydroxide, benzyltributylammonium chloride, tetra-n-butylammonium chloride, bromide, iodide or hydroxide, cetyltrimethylammonium chloride or bromide, tetra-n-pentylammonium chloride, tetra-n-hexylammonium chloride or bromide, tetrabutylammonium hydrogen sulfate, benzyltributylammonium chloride, trimethyloctadecylammonium bromide, tributylhexadecylphosphonium bromide, ethyltriphenylphosphonium bromide, tetraphenylphosphonium bromide, tetrabutylphosphonium chloride or the various crown ethers such as 1,4,7,10,13-pentaoxa[13]orthocyclophane, 1,4,7,14,17,20-hexaoxa[7,7]orthocyclophane, 1,4,7,10,17,20,23,26-octaoxa[10,10]-orthocyclophane, 1,4,7,14,23-pentaoxa[7,2]orthocyclo[2](2,6)-pyridinophane, 2,5,8,15,18,21-hexaoxatricyclo[20,4,0,0$^{9,14}$]-hexacosane, 1,4,7,10-tetraoxacyclododecane, 1,4,7,10,13-pentaoxacyclopentadecane, 1,4,7,10,13,16-hexaoxacyclooctadecane, N-phenyl-13-aza-1,4,7,10-tetraoxacyclopentadecane, 1,13-bis(8-quinolyl)-1,4,7,10,13-pentaoxatridecane, 1,4,10-trioxa-7,13-diazacyclopentadecane, 1,7,10,16-tetraoxa-4,13-diazacyclooctadecane, 4,13-didecyl-1,7,10,16-tetraoxa-4,13-diazacyclooctadecane, 1,7,10,13,19-pentaoxa-4,16-diazacycloheneicosane, 4,7,13,18-tetraoxa-1,10-diazabicyclo-(8,5,5)-eicosane, 4,7,13,16,21-pentaoxa-1,10-diazabicyclo-(8,8,5)-tricosane, 4,7,13,16,21,24-hexaoxa-1,10-diazabicyclo-(8,8,8)-hexacosane, 5,6-benzo-4,7,13,16,21,24-hexaoxa-1,10-diazabicyclo(8,8,8)hexacosane, 5,6-14,15-dibenzo-4,7,13,16,21,24-hexaoxa-1,10-diazabicyclo-(8,8,8)-hexacosane, 5,6-14,15-dicyclohexylene-4,7,13,16,21,24-hexaoxa-1,10-diazabicyclo-(8,8,8)-hexacosane and 5-decyl-4,7,13,16,21,24-hexaoxa-1,10-diazabicyclo(8,8,8)-hexacosane.

It was surprising that these good results were obtained, not only in acetone, but also in other organic liquids, which, of course, must not enter into any unwanted reaction with the silane and, because of the sensitivity of the alkoxy group(s) to hydrolysis, must be substantially anhydrous and able at least partly to dissolve the iodide or silane component.

Suitable liquids, which can also be designated as solvents or diluents, are cyclic or open chain ethers, preferably tetrahydrofuran, dioxane, trioxane, diethyl, dipropyl and dibutyl ethers and ethyleneglycol dimethyl ether; chlorohydrocarbons, preferably methylene chloride, chloroform, 1,2-dichloroethane, 1,1,1-trichloroethane, trichloroethylene and chlorobenzene; aliphatic and aromatic nitro compounds, preferably nitromethane, nitroethane and nitrobenzene; aliphatic nitriles, preferably acetonitrile or propionitrile; or also dimethylformamide, dimethylsulfoxide, acetone, diethyl ketone, methylethyl ketone and especially lower alcohols such as methanol, ethanol, n- and i-propanol, n- and i-butanol and pentanol. The use of alcohols particularly represents an important aspect of the process of the invention, since it means a considerable reduction of the preparative overall cost if after the esterification of the appropriate precursor—in general this is the corresponding chloroalkylchlorosilane—isolation of the chloroalkylalkoxysilane can be dispensed with, and instead, immediately after alcoholysis and removal of the liberated hydrogen chloride and possibly likewise after addition of a further excess of alcohol, the exchange of chlorine for iodine is completed at room temperature, but preferably at an elevated temperature up to 250° C. and at atmospheric pressure or optionally at above-atmospheric pressure up to 200 bar. The pure (iodoalkyl)alkoxysilane can subsequently be obtained by distillation after removal of the sodium chloride formed and the excess iodide and the solvent used.

Typical silanes which can be prepared by the process of the present invention are, for example, I-(CH$_2$)$_3$-Si(OC$_2$H$_5$)$_3$; I-(CH$_2$)$_3$-Si(OCH$_3$)$_3$; I-(CH$_2$)$_2$-Si(OC$_2$H$_5$)$_3$; I-CH$_2$-Si(OC$_2$H$_5$)$_3$; I-(CH$_2$)$_2$-Si(OC$_2$H$_5$)$_3$; I-CH$_2$-Si(OC$_2$H$_5$)$_3$; I-CH$_2$-Si(OCH$_3$)$_3$; I-(CH$_2$)$_3$-Si(OC$_2$H$_5$)$_2$(CH$_3$); I-(CH$_2$)$_3$-Si(OC$_2$H$_5$)-(C$_6$H$_5$)$_2$;

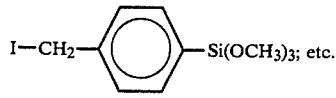

A favorable embodiment of the invention provides that the compounds of formula (1) are prepared with the use of NaI or KI in the alcohol corresponding to the particular alkoxy, methoxyethoxy or ethoxyethoxy group attached to the silicon.

In the framework of the present invention it is also preferred that the substituents R$^2$, R$^3$ and R$^4$ have the same meaning.

Although for economic reasons anhydrous NaI or KI are preferably used as iodine donors, in principle other alkali metal iodides or also alkaline earth metal and ammonium iodides such as LiI, MgI$_2$, CaI$_2$, SrI$_2$, BaI$_2$, NH$_4$I, (H$_3$C)$_4$NI may also be used. A quantitative conversion can be achieved even with a stoichiometric molar ratio of iodine donor: (chloroorganyl)alkoxysilane. For a shorter overall reaction time, however, a molar ratio between 1:1 and 2:1 is preferred.

The process disclosed is further illustrated below by means of representative examples. It can be seen from these examples that the invention can be put into practice within the scope claimed. In principle, the starting materials needed are: a chloro- or bromoorganyl silicon compound with at least one alkoxy group attached to the silicon, an inorganic iodine donor and an onium compound substituted with organic residues or a crown ether as catalyst and a solubilizing agent for these reactants.

EXAMPLE 1

300.5 g (2.00 mol) NaI and 7.11 g (16.09 mmol=about 0.80 mol % calculated on NaI) of a phase transfer catalyst obtainable from Merck (Darmstadt) under the name of "Aliquat 336", consisting essentially of tricaprylmethylammonium chloride (mean molecular weight 442), were brought together in 300 ml of dry ethanol. Then 355.4 g (1.67 mol) ClCH$_2$-Si(OC$_2$H$_5$)$_3$ were added to this suspension at room temperature within 10 minutes and heated with stirring to reflux temperature. After 6 hours heating none of the starting silane could be detected by NMR spectroscopy. The alcohol was then distilled off, first at normal pressure and later at 50-50 mbar and the remaining liquid separated from the solid substance present by centrifuging and decanting. After washing with 2×100 ml methylene chloride and combining the centrifugates, the methylene chloride present was distilled off at normal pressure and the ICH$_2$Si(OC$_2$H$_5$)$_3$ was distilled in vacuum (B.P.$_{30\ mbar}$:113° C.). Yield: 436.9 g (86.0% of theory).

EXAMPLE 2

538.7 g (16.81 mol) CH$_3$OH was added in a period of 2.5 hours to 1080 g (5.095 mol) Cl(CH$_2$)$_3$SiCl$_3$ while the liberated hydrogen chloride was blown out with nitrogen. At the end of the addition, nitrogen was blown through the reaction solution for a further 2 hours and the hydrochloric acid still present was neutralized by the addition of 5.5 g (0.1 mol) NaOCH$_3$. Then 300 ml dry methanol, 916.4 g (6.11 mol) NaI and 60.9 g (0.12 mol=about 2 mol% calculated on NaI) tributylhexadecylphosphonium bromide was added directly and heated for 6 hours under reflux. Further processing was carried out analogously to Example 1: after removal of the methanol, separating off of the solid and washing with 2×250 ml methylene chloride followed by evaporating off of this and subsequent distillation of the product (B.P.$_{3\ mbar}$:95° C.) in vacuum, 1175.4 g (79.5% of theory) I(CH$_2$)$_3$Si(OCH$_3$)$_3$ was obtained.

EXAMPLE 3

After 7.5 hours reaction of 120 g (0.341 mol) of

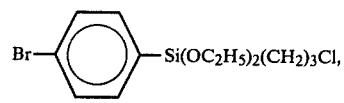

62.3 g (0.375 mol) KI and 0.854 g (3.75 mmol) benzyltriethylammonium chloride in 150 ml boiling acetonitrile, analogously to Example 1, 121,2 g (80.2% of theory) of

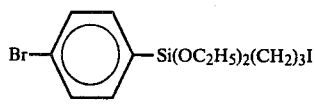

(B.P.$_{0.05\ mbar}$:120° C.) was obtained.

EXAMPLE 4

After 5 hours reaction of 188.3 g (0.763 mol) of

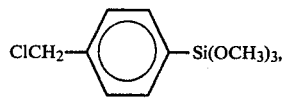

125.82 g (0.839 mol) NaI and 1.72 g (3.89 mmol) "Aliquat 336" in 200 ml dry acetone, analogously to Example 1, 201.03 g (77.9% of theory) of

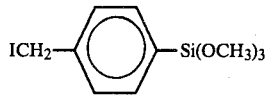

(B.P.$_{0.5}$ mbar: 117° C.) was obtained.

EXAMPLE 5

200 g (0.44 mol) Cl(CH$_2$)$_{18}$Si(OC$_2$H$_5$)$_3$, 100.5 g (0.50 mol) N(CH$_3$)$_4$I and 3.49 g (3 mol % calculated on the iodide component) of a crown ether of the formula C$_{12}$H$_{24}$O$_6$ were brought together in 250 ml dry ethanol. The mixture was stirred for 8 hours under reflux and then freed from sparingly soluble components. After removal of the ethanol by distillation on a rotary evaporator, the mixture was again centrifuged and the solid residue washed with 2×100 ml n-hexane. The wash solution and the centrifugate were then distilled first under normal pressure and then under high vacuum on a short path still, whereby the desired product I(CH$_2$)$_{18}$Si(OC$_2$H$_5$)$_3$ distilled over at a heating mantle temperature of 225°–230° C. (0.05 mbar). Yield: 179.08 g (75.0% of theory).

When the catalyst is a quaternary ammonium, phosphonium, arsonium, antimonium or tertiary sulfonium salt, suitable alkyl substituents are defined as:

A linear or branched alkyl group with 1–20 C-atoms; suitable aryl substituents are Phenyl, toluyl, xylyl, naphtyl and suitable aralkyl substituents are Benzyl, phenylethyl. Similarly, suitable organic anions are Acetate, propionate, benzoate, tetraphenylborate and suitable inorganic anions are Fluoride, chloride, bromide, iodide, hydroxide, sulfate, hydrogen sulfate, nitrate, phosphate.

What is claimed is:

1. Process for the manufacture of an (iodoorganyl)alkoxysilane of the formula:

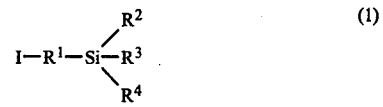

in which R$^1$ represents straight or branched chain alkylene having 1 to 20 carbon atoms, cycloalkylene having 5 to 8 carbon atoms or a unit of the type:

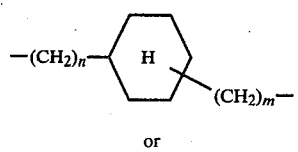

or

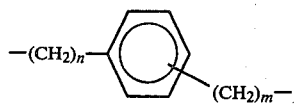

wherein n is a number between 1 and 6 of methylene groups in the chain attached to the halogen and m is a number from 0 to 6, R$^2$ represents alkoxy having 1 to 5 carbon atoms, methoxyethoxy or ethoxyethoxy, R$^3$ and R$^4$ may be the same or different and have the same meaning as R$^2$ or represent branched or linear alkyl having 1 to 10 carbon atoms, phenyl or phenyl substituted with halogen, which process comprises reacting the corresponding chlorine or bromine silane compound with stoichiometric to double molar quantities of alkali, alkaline earth or ammonium iodide in the presence of 0.01 to 5 mol % of a quarternary ammonium, phosphonium, arsonium, antimonium or tertiary sulfonium salt with alkyl, aryl or aralkyl substitutents and an organic or inorganic anion or a crown ether, in an organic liquid or mixture of organic liquids which is substantially inert towards the silane and is able to dissolve at least partly the iodide or silane component.

2. The process according to claim 1 wherein the organic liquid or mixture of organic liquids is a cyclic or open chain ether, a chlorohydrocarbon, an aliphatic or aromatic nitro compound, an aliphatic nitrile, dimethylformamide, dimethylsulfoxide, acetone, diethyl ketone, methylethyl ketone or a lower alcohol.

3. The process according to claim 1 wherein the reaction is carried out in tetrahydrofuran, dioxane, trioxane, diethyl, dipropyl or dibutyl ether, ethylene glycol dimethyl ether, methylene chloride, chloroform, 1,2-dichloroethane, 1,1,1-trichloroethane, trichloroethylene, chlorobenzene, nitromethane, nitroethane, nitrobenzene, acetonitrile, propionitrile, methanol, ethanol, n- or i-propanol, n- or i-butanol or pentanol.

4. The process according to claim 1, 2 or 3 wherein the compounds of formula (1) are prepared by the use of sodium iodide or potassium iodide in the alcohol corresponding to the particular alkoxy, methoxy or ethoxyethoxy group attached to the silicon.

5. The process according to claim 1, 2, or 3 wherein the compounds of formula (1) are prepared by the use of sodium iodide or potassium iodide in the alcohol corresponding to the particular alkoxy, methoxy, or ethoxyethoxy group attached to the silicon and wherein R$^2$, R$^3$ and R$^4$ have the same meaning.

6. The process according to claim 1, 2 or 3 wherein R$^2$, R$^3$ and R$^4$ have the same meaning.

* * * * *